United States Patent
Callot et al.

(10) Patent No.: US 12,059,504 B2
(45) Date of Patent: Aug. 13, 2024

(54) METHOD FOR THE PRODUCTION OF SUPERABSORBENTS

(71) Applicant: BASF SE, Ludwigshafen (DE)

(72) Inventors: Rene Callot, Antwerp (BE); Ruediger Funk, Ludwigshafen (DE); Marco Krueger, Ludwigshafen (DE); Thomas Pfeiffer, Ludwigshafen (DE); Karl Possemiers, Antwerp (BE); Juergen Schroeder, Ludwigshafen (DE); Matthias Weismantel, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 769 days.

(21) Appl. No.: 17/272,364

(22) PCT Filed: Sep. 17, 2019

(86) PCT No.: PCT/EP2019/074782
§ 371 (c)(1),
(2) Date: Mar. 1, 2021

(87) PCT Pub. No.: WO2020/064411
PCT Pub. Date: Apr. 2, 2020

(65) Prior Publication Data
US 2021/0338882 A1 Nov. 4, 2021

(30) Foreign Application Priority Data
Sep. 28, 2018 (EP) .................................... 18197563

(51) Int. Cl.
| | | |
|---|---|---|
| *C08F 220/06* | (2006.01) | |
| *A61L 15/60* | (2006.01) | |
| *B01J 20/26* | (2006.01) | |
| *B08B 1/02* | (2006.01) | |
| *B08B 1/16* | (2024.01) | |
| *B08B 1/20* | (2024.01) | |
| *C08F 6/00* | (2006.01) | |
| *C08J 3/24* | (2006.01) | |

(52) U.S. Cl.
CPC ............. *A61L 15/60* (2013.01); *B01J 20/261* (2013.01); *B08B 1/165* (2024.01); *B08B 1/20* (2024.01); *C08F 220/06* (2013.01); *C08J 3/245* (2013.01); *B01J 2220/68* (2013.01); *C08F 6/008* (2013.01)

(58) Field of Classification Search
None
See application file for complete search history.

(56) References Cited

U.S. PATENT DOCUMENTS

| | | |
|---|---|---|
| 6,667,372 B1 | 12/2003 | Miyake et al. |
| 8,362,174 B2 | 1/2013 | Funk et al. |
| 2014/0114035 A1* | 4/2014 | Nogi ........................... C08J 3/12 526/212 |
| 2015/0119531 A1* | 4/2015 | Bauduin ................. A61L 15/60 525/329.9 |

FOREIGN PATENT DOCUMENTS

| | | |
|---|---|---|
| CN | 102762616 A | 10/2012 |
| EP | 2700667 A1 | 2/2014 |
| JP | 10250821 A * | 9/1998 |
| JP | H10250821 A | 9/1998 |
| JP | 2001131218 A | 5/2001 |
| WO | WO-2008/087114 A1 | 7/2008 |
| WO | WO-2010/139680 A2 | 12/2010 |
| WO | WO-2014/005860 A1 | 1/2014 |
| WO | WO-2015/163517 A1 | 10/2015 |

OTHER PUBLICATIONS

International Application No. PCT/EP2019/074782, International Search Report, dated Dec. 10, 2019.
Graham, et al., "Chapter 3: Commercial Processes for the Manufacture of Superabsorbent Polymers", Modern Superabsorbent Polymer Technology, ed. Buchholz, et al., 2nd Edition, 1998, pp. 69-117.

* cited by examiner

*Primary Examiner* — Richard A Huhn
(74) *Attorney, Agent, or Firm* — James J. Napoli

(57) ABSTRACT

A process for producing superabsorbent particles by polymerizing a monomer solution or suspension, comprising drying of the resultant aqueous polymer gel in an air circulation belt drier, grinding, classifying, and optionally thermal surface postcrosslinking, wherein the aqueous polymer gel is introduced into the air circulation belt drier by means of an oscillating conveyor belt, the underside of the revolving conveyor belt is freed of adhering polymer gel by means of at least one stripper device, and the underside of the revolving conveyor belt is sprayed with water.

13 Claims, No Drawings

METHOD FOR THE PRODUCTION OF SUPERABSORBENTS

CROSS-REFERENCE TO RELATED APPLICATIONS

This is the U.S. national phase of International Application No. PCT/EP2019/074782, filed Sep. 17, 2019, which claims the benefit of European Patent Application No. 18197563.2, filed on Sep. 28, 2018.

The present invention relates to a process for producing superabsorbent particles by polymerizing a monomer solution or suspension, comprising drying of the resultant aqueous polymer gel in an air circulation belt drier, grinding, classifying, and optionally thermal surface postcrosslinking, wherein the aqueous polymer gel is introduced into the air circulation belt drier by means of an oscillating conveyor belt, the underside of the revolving conveyor belt is freed of adhering polymer gel by means of at least one stripper device, and the underside of the revolving conveyor belt is sprayed with water.

Superabsorbents are used to produce diapers, tampons, sanitary napkins and other hygiene articles, but also as water-retaining agents in market gardening. Superabsorbents are also referred to as water-absorbing polymers.

The production of superabsorbents is described in the monograph "Modern Superabsorbent Polymer Technology", F. L. Buchholz and A. T. Graham, Wiley-VCH, 1998, pages 71 to 103.

The properties of the superabsorbents can be adjusted, for example, via the amount of crosslinker used. With increasing amount of crosslinker, the centrifuge retention capacity (CRC) falls and the absorption under a pressure of 21.0 $g/cm^2$ (AUL0.3 psi) passes through a maximum.

To improve the performance properties, for example gel bed permeability (GBP) and absorption under a pressure of 49.2 $g/cm^2$ (AUL0.7 psi), superabsorbent particles are generally surface postcrosslinked. This increases the level of crosslinking of the particle surface, which can at least partly decouple the absorption under a pressure of 49.2 $g/cm^2$ (AUL0.7 psi) and the centrifuge retention capacity (CRC). This surface postcrosslinking can be performed in the aqueous gel phase. Preferably, however, polymer particles (base polymer), having been dried, ground and sieved off, are surface coated with a surface postcrosslinker and thermally surface postcrosslinked. Crosslinkers suitable for that purpose are compounds which can form covalent bonds with at least two carboxylate groups of the polymer particles.

WO 2008/087114 A1, WO 2010/139680 A2 and EP 2 700 667 A1 describe the loading of the transport belts of air circulation belt driers with aqueous polymer gel by means of oscillating conveyor belts.

It was an object of the present invention to provide an improved process for producing superabsorbents, especially simplified cleaning of the oscillating conveyor belt used and lower mechanical stress on the conveyor belt itself.

The object was achieved by a process for producing superabsorbents by polymerizing a monomer solution or suspension comprising
  a) at least one ethylenically unsaturated monomer which bears acid groups and is at least partly neutralized,
  b) at least one crosslinker,
  c) at least one initiator,
  d) optionally one or more ethylenically unsaturated monomers copolymerizable with the monomers mentioned under a) and
  e) optionally one or more water-soluble polymers, comprising drying of the resultant aqueous polymer gel in an air circulation belt drier, grinding, classifying, and optionally thermal surface postcrosslinking, wherein the aqueous polymer gel is introduced into the air circulation belt drier by means of an oscillating conveyor belt, the underside of the revolving conveyor belt is freed of adhering polymer gel by means of at least one stripper device, and the underside of the revolving conveyor belt is sprayed with water.

The underside of the revolving conveyor belt is the outside of the conveyor belt which, after deflection, is dosed again with polymer gel. The top side of the revolving conveyor belt is the inside of the conveyor belt that is not supposed to come into contact with polymer gel.

The distance of the stripper device from the discharge end of the oscillating conveyor belt is preferably less than 20% of the length of the oscillating conveyor belt, more preferably less than 10% of the length of the oscillating conveyor belt, most preferably less than 5% of the length of the oscillating conveyor belt, where the length of the oscillating conveyor belt is the distance of the pivot axis from the discharge end.

The stripper device is not subject to any restrictions. Suitable examples are brushes arranged transverse to the running direction. It is also possible to use a scraper. A scraper is a stripper device made of a nonflexible material which is arranged transverse to the conveying direction. An example of a suitable nonflexible material is polytetrafluoroethylene. In order to avoid damage to the conveyor belt, the scraper should have minimum direct contact, if any, with the conveyor belt. The scraper should be inclined with respect to the running direction of the revolving conveyor belt. This promotes the peeling-off of the adhering polymer gel, and prevents backup between conveyor belt and scraper. The stripped-off polymer gel typically falls onto the conveyor belt of the air circulation belt drier.

The scraper is preferably inclined at 5° to 45°, more preferably at 10° to 35°, very particularly at 15° to 25°, relative to the horizontal counter to the running direction of the conveyor belt. The distance of the scraper from the underside of the revolving conveyor belt is preferably 0.1 to 5 mm, more preferably 0.2 to 2 mm, most preferably 0.5 to 1.5 mm.

The distance of the spray nozzles from the discharge end of the oscillating conveyor belt is preferably 1% to 50% of the length of the oscillating conveyor belt, more preferably 2% to 30% of the length of the oscillating conveyor belt, most preferably 3% to 10% of the length of the oscillating conveyor belt, where the length of the oscillating conveyor belt is the distance of the pivot axis from the discharge end.

The distance of the spray nozzles from the conveyor belt is preferably 5 to 50 cm, more preferably 10 to 30 cm and most preferably 15 to 25 cm.

The liquid is preferably sprayed on by means of at least one two-phase nozzle, more preferably by means of at least two two-phase nozzles.

Two-phase nozzles enable atomization into fine droplets or a spray mist. The atomization form employed is a circular or else elliptical solid or hollow cone. Two-phase nozzles may be configured with external mixing or internal mixing. In the case of the externally mixing two-phase nozzles, liquid and atomizer gas leave the nozzle head through separate orifices. They are mixed in the spray jet only after leaving the spray nozzle. This enables independent regulation of droplet size distribution and throughput over a wide range. The spray cone of the spray nozzle can be adjusted via the air cap setting. In the case of the internally mixing two-phase nozzle, liquid and atomizer gas are mixed within the spray nozzle and the biphasic mixture leaves the nozzle head through the same bore (or through a plurality of parallel bores). In the case of the internally mixing two-phase nozzle, the quantitative ratios and pressure conditions are more highly coupled than in the case of the externally mixing spray nozzle. Small changes in the throughput therefore lead to a change in the droplet size distribution. The adjustment to the desired throughput is effected through the selected cross section of the nozzle bore.

An example of a useful atomizer gas is compressed air at 0.5 bar or more. The droplet size can be adjusted individually via the nozzle geometry, the nozzle type, the ratio of water mass flow rate to atomizer gas mass flow rate, and gas and water pressure.

The amount of the water used for spraying is preferably from 2 to 20 kg/h, more preferably from 6 to 16 kg/h, most preferably from 8 to 12 kg/h.

The weight ratio of atomizer gas to water is preferably from 2 to 20, more preferably from 6 to 16 and most preferably from 8 to 12.

When too little water is used, the conveyor belt is wetted only inadequately. When too much water is used, excess water drips onto the perforated plates of the air circulation belt drier and leads to blockages there. The use of two-phase nozzles additionally improves the distribution of the water by preventing larger droplets.

In a preferred embodiment of the present invention, there is at least one spray nozzle beyond the strip device in the running direction of the conveyor belt. This prevents water from dripping off the stripper device onto the conveyor belt of the air circulation belt drier.

In a further preferred embodiment of the present invention, there is at least one spray nozzle upstream of the conveyor belt of the air circulation belt drier. This also prevents water from dripping onto the conveyor belt of the air circulation belt drier.

The conveyor belt has a length of preferably 2 to 10 m, more preferably from 2.5 to 8 m, most preferably from 3 to 6 m, where the length of the conveyor belt is the distance of the pivot axis from the discharge end.

The conveyor belt has a width of preferably 0.5 to 1.5 m, more preferably of 0.6 to 1.2 m, most preferably of 0.7 to 0.9 m.

It is possible to use the conveyor belts that are customary for this purpose. The surface of the conveyor belts, i.e. the side that comes into contact with the polymer gel, should be water repellent and, at 23° C., have a contact angle with respect to water of preferably at least 60°, more preferably at least 80°, most preferably at least 100°. The contact angle is a measure of the wetting behavior and is measured to DIN 53900.

The water content of the polymer gel on the conveyor belt is preferably from 20 to 80% by weight, more preferably from 30 to 70% by weight, most preferably from 40 to 60% by weight.

The temperature of the polymer gel on the conveyor belt is preferably from 60 to 105° C., more preferably from 70 to 100° C. and most preferably from 80 to 95° C.

The present invention is based on the finding that warm polymer gel adhering to the oscillating conveyor belt dries out very easily. The dried polymer gel can be removed from the conveyor belt only with great difficulty. Already dried polymer gel is often the cause of further caking. Spraying with water can keep the polymer gel moist and prevent drying.

The production of the superabsorbents is described in detail hereinafter:

The superabsorbents are produced by polymerizing a monomer solution or suspension, and are typically water-insoluble.

The monomers a) are preferably water-soluble, i.e. their solubility in water at 23° C. is typically at least 1 g/100 g of water, preferably at least 5 g/100 g of water, more preferably at least 25 g/100 g of water and most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 02/055469 A1, WO 03/078378 A1 and WO 2004/035514 A1. A suitable monomer a) is, for example, an acrylic acid purified according to WO 2004/035514 A1 and comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, and preferably at least 10 ppm by weight, more preferably at least 30 ppm by weight and especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 03/104299 A1, WO 03/104300 A1, WO 03/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 02/032962 A2.

Preferred crosslinkers b) are pentaerythrityl triallyl ether, tetraallyloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or propoxylated glycerols which have been esterified with acrylic acid or methacrylic acid to give di- or triacrylates, as described, for example, in WO 03/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3-to 5-tuply ethoxylated and/or propoxylated glycerol, especially the triacrylate of 3-tuply ethoxylated glycerol.

The amount of crosslinker b) is preferably 0.05% to 1.5% by weight, more preferably 0.1% to 0.8% by weight and most preferably 0.15% to 0.5% by weight, calculated in each case on the basis of the total amount of monomer a) used. With rising crosslinker content, centrifuge retention capacity (CRC) falls and the absorption under a pressure of 21.0 g/cm$^2$ passes through a maximum.

Initiators c) used may be all compounds which generate free radicals under the polymerization conditions, for example thermal initiators, redox initiators or photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is preferably the disodium salt of 2-hydroxy-2-sulfonatoacetic acid or a mixture of the sodium salt of 2-hydroxy-2-sulfinatoacetic acid, the disodium salt of 2-hydroxy-2-sulfonatoacetic acid and sodium bisulfite. Such mixtures are obtainable as Bruggolite® FF6 and Brüggolite® FF7 (Brüggemann Chemicals; Heilbronn; Germany).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methyl cellulose or hydroxyethyl cellulose, gelatin, polyglycols or polyacrylic acids, preferably starch, starch derivatives and modified cellulose.

Typically, an aqueous monomer solution is used. The water content of the monomer solution is preferably from 40% to 75% by weight, more preferably from 45% to 70% by weight and most preferably from 50% to 65% by weight. It is also possible to use monomer suspensions, i.e. monomer solutions with monomer a) over and above the solubility, for example sodium acrylate. As the water content rises, the energy expenditure in the subsequent drying rises and, as the water content falls, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

Suitable reactors for the polymerization are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on the belt is described, for example, in DE 38 25 366 A1 and U.S. Pat. No. 6,241,928. Polymerization in a belt reactor forms a polymer gel which has to be comminuted, for example in an extruder or kneader.

To improve the drying properties, the comminuted polymer gel obtained by means of a kneader can additionally be extruded.

The acid groups of the resulting polymer gels have typically been partly neutralized. Neutralization is preferably carried out at the monomer stage. This is typically accomplished by mixing in the neutralizing agent as an aqueous solution or else preferably as a solid. The degree of neutralization is preferably from 25 to 85 mol %, more preferably from 30 to 80 mol % and most preferably from 40 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof. Solid carbonates and hydrogencarbonates can also be introduced here in encapsulated form, preferably into the monomer solution directly prior to the polymerization, into the polymer gel during or after the polymerization and prior to the drying thereof. The encapsulation is effected by coating of the surface with an insoluble or only gradually soluble material (for example by means of film-forming polymers, of inert inorganic materials or of fusible organic materials) which delays the dissolution and reaction of the solid carbonate or hydrogencarbonate to such a degree that carbon dioxide is not released until during the drying and the superabsorbent formed has high internal porosity.

Optionally, a surfactant can be added to the monomer solution before or during the polymerization and the monomer solution can then be foamed before or during the polymerization with an inert gas or water vapor or by vigorous stirring. The surfactant may be anionic, cationic, zwitterionic or else nonionic. Preference is given to using a skin-friendly surfactant.

The polymer gel is then typically dried with an air circulation belt drier until the residual moisture content is preferably 0.5 to 10% by weight, more preferably 1 to 6% by weight and most preferably 1.5 to 4% by weight, the residual moisture content being determined by EDANA recommended test method No. WSP 230.2-05 "Mass Loss Upon Heating". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size are obtained ("fines"). The solids content of the polymer gel before the drying is preferably from 25% to 90% by weight, more preferably from 35% to 70% by weight, most preferably from 40% to 60% by weight. Subsequently, the dried polymer gel is crushed and optionally coarsely comminuted.

Thereafter, the dried polymer gel is typically ground and classified, and the apparatus used for grinding may typically be single- or multistage roll mills, preferably two- or three-stage roll mills, pin mills, hammer mills or vibratory mills.

The average particle size of the polymer particles removed as the product fraction is preferably from 150 to 850 µm, more preferably from 250 to 600 µm, very particularly from 300 to 500 µm. The average particle size of the product fraction may be determined by means of EDANA recommended test method No. WSP 220.2 (05) "Particle Size Distribution", where the proportions by mass of the screen fractions are plotted in cumulative form and the average particle size is determined graphically. The average particle size here is the value of the mesh size which arises for a cumulative 50% by weight.

The proportion of polymer particles having a particle size of greater than 150 µm is preferably at least 90% by weight, more preferably at least 95% by weight, most preferably at least 98% by weight.

Polymer particles with too small a particle size lower the gel bed permeability (GBP). The proportion of excessively small polymer particles ("fines") should therefore be small.

Excessively small polymer particles are therefore typically removed and recycled into the process, preferably before, during or immediately after the polymerization, i.e. prior to the drying of the polymer gel. The excessively small polymer particles can be moistened with water and/or aqueous surfactant before or during the recycling.

It is also possible to remove excessively small polymer particles in later process steps, for example after the surface postcrosslinking or another coating step. In this case, the excessively small polymer particles recycled are surface postcrosslinked or coated in another way, for example with fumed silica.

The proportion of polymer particles having a particle size of at most 850 µm is preferably at least 90% by weight, more preferably at least 95% by weight, most preferably at least 98% by weight.

The proportion of polymer particles having a particle size of at most 600 µm is preferably at least 90% by weight, more preferably at least 95% by weight, most preferably at least 98% by weight.

Polymer particles of excessively large particle size lower the free swell rate. The proportion of excessively large polymer particles should therefore likewise be low. Excessively large polymer particles are therefore typically removed and recycled into the grinding.

To further improve the properties, the polymer particles can be thermally surface postcrosslinked. Suitable surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1, 2-oxazolidinone and derivatives thereof, such as 2-hydroxyethyl-2-oxazolidinone, in DE 198 07 502 A1, bis- and poly-2-oxazolidinones in DE 198 07 992 C1, 2-oxotetrahydro-1,3-oxazine and derivatives thereof in DE 198 54 573 A1, N-acyl-2-oxazolidinones in DE 198 54 574 A1, cyclic ureas in DE 102 04 937 A1, bicyclic amido acetals in DE 103 34 584 A1, oxetanes and cyclic ureas in EP 1 199 327 A2 and morpholine-2,3-dione and derivatives thereof in WO 03/031482 A1.

Preferred surface postcrosslinkers are ethylene carbonate, ethylene glycol diglycidyl ether, reaction products of polyamides with epichlorohydrin and mixtures of propylene glycol and butane-1,4-diol.

Very particularly preferred surface postcrosslinkers are 2-hydroxyethyl-2-oxazolidinone, 2-oxazolidinone and propane-1,3-diol.

In addition, it is also possible to use surface postcrosslinkers which comprise additional polymerizable ethylenically unsaturated groups, as described in DE 37 13 601 A1.

The amount of surface postcrosslinker is preferably 0.001% to 3% by weight, more preferably 0.02% to 1% by weight and most preferably 0.05% to 0.2% by weight, based in each case on the polymer particles.

The surface postcrosslinking is typically performed in such a way that a solution of the surface postcrosslinker is sprayed onto the dried polymer particles. After the spray application, the polymer particles coated with surface postcrosslinker are surface postcrosslinked and dried, and the surface postcrosslinking reaction can take place both before and during the drying.

The spray application of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers have a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; USA) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The penetration depth of the surface postcrosslinker into the polymer particles can be adjusted via the content of nonaqueous solvent and total amount of solvent.

When exclusively water is used as the solvent, a surfactant is advantageously added. This improves the wetting characteristics and reduces the tendency to form lumps. However, preference is given to using solvent mixtures, for example isopropanol/water, 1,3-propanediol/water and propylene glycol/water, where the mixing ratio in terms of mass is preferably from 20:80 to 40:60.

The surface postcrosslinking is preferably performed in contact driers, more preferably paddle driers, most preferably disk driers. Suitable driers are, for example, Hosokawa Bepex® Horizontal Paddle Dryer (Hosokawa Micron GmbH; Leingarten; Germany), Hosokawa Bepex® Disk Dryer (Hosokawa Micron GmbH; Leingarten; Germany), Holo-Flite® driers (Metso Minerals Industries Inc.; Danville; USA) and Nara Paddle Dryer (NARA Machinery Europe; Frechen; Germany). Moreover, fluidized bed driers may also be used.

The surface postcrosslinking can be effected in the mixer itself, by heating the jacket or blowing in warm air. Equally suitable is a downstream drier, for example a tray drier, a rotary tube oven or a heatable screw. It is particularly advantageous to effect mixing and thermal surface postcrosslinking in a fluidized bed drier.

Preferred reaction temperatures are in the range of 100 to 250° C., preferably 110 to 220° C., more preferably 120 to 210° C., most preferably 130 to 200° C. The preferred dwell time at this temperature is preferably at least 10 minutes, more preferably at least 20 minutes, most preferably at least 30 minutes, and typically at most 60 minutes.

In a preferred embodiment of the present invention, the polymer particles are cooled after the surface postcrosslinking. The cooling is preferably performed in contact coolers, more preferably paddle coolers and most preferably disk coolers. Suitable coolers are, for example, Hosokawa Bepex® Horizontal Paddle Cooler (Hosokawa Micron GmbH; Leingarten; Germany), Hosokawa Bepex® Disc Cooler (Hosokawa Micron GmbH; Leingarten; Germany), Holo-Flite® coolers (Metso Minerals Industries Inc.; Danville; USA) and Nara Paddle Cooler (NARA Machinery Europe; Frechen; Germany). Moreover, fluidized bed coolers may also be used.

In the cooler, the polymer particles are cooled to preferably 40 to 90° C., more preferably 45 to 80° C., most preferably 50 to 70° C.

Subsequently, the surface postcrosslinked polymer particles can be classified again, with excessively small and/or excessively large polymer particles being removed and recycled into the process.

To further improve the properties, the surface postcrosslinked polymer particles can be coated or remoisturized.

The remoisturizing is preferably performed at 40 to 120° C., more preferably at 50 to 110° C., most preferably at 60 to 100° C. At excessively low temperatures the polymer particles tend to form lumps, and at higher temperatures water already evaporates to a noticeable degree. The amount of water used for remoisturizing is preferably from 1% to 10% by weight, more preferably from 2% to 8% by weight and most preferably from 3% to 5% by weight. The remoisturizing increases the mechanical stability of the polymer particles and reduces their tendency to static charging. The remoisturizing is advantageously performed in a cooler after the thermal surface postcrosslinking.

Suitable coatings for improving the swell rate and the gel bed permeability (GBP) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20. Suitable coatings for dust binding, for reducing the tendency to caking and for increasing the mechanical stability are polymer dispersions as described in EP 0 703 265 B1, and waxes as described in U.S. Pat. No. 5,840,321.

Subsequently, the coated and/or remoisturized polymer particles can be classified again, with removal of excessively small and/or excessively large polymer particles and recycling into the process.

The present invention further provides hygiene articles comprising superabsorbents produced by the process of the invention.

Methods:

The standard test methods described hereinafter and designated "WSP" are described in: "Standard Test Methods for the Nonwovens Industry", 2005 edition, published jointly by the Worldwide Strategic Partners EDANA (Herrmann-Debrouxlaan 46, 1160 Oudergem, Belgium, www.edana.org) and INDA (1100 Crescent Green, Suite 115, Cary, North Carolina 27518, USA, www.inda.org). This publication is obtainable both from EDANA and from INDA.

The measurements should, unless stated otherwise, be conducted at an ambient temperature of 23±2° C. and a relative air humidity of 50±10%. The water-absorbing polymer particles are mixed thoroughly before the measurement.

Centrifuge Retention Capacity

Centrifuge retention capacity (CRC) is determined by EDANA recommended test method No. WSP 241.2 (05) "Fluid Retention Capacity in Saline, After Centrifugation".

Extractables

The content of extractables of the water-absorbing polymer particles is determined by EDANA recommended test method No. WSP 270.2 (05) "Extractable".

EXAMPLES

Example 1

By continuously mixing deionized water, 50% by weight sodium hydroxide solution and acrylic acid, an acrylic acid/sodium acrylate solution was prepared such that the degree of neutralization corresponded to 71.3 mol %. The solids content of the monomer solution was 38.8% by weight.

The polyethylenically unsaturated crosslinker used was polyethylene glycol-400 diacrylate (diacrylate proceeding from a polyethylene glycol with a mean molar mass of 400 g/mol). The amount used was 2 kg of crosslinker per t of monomer solution.

To initiate the free-radical polymerization, per t of monomer solution, 1.03 kg of a 0.25% by weight aqueous hydrogen peroxide solution, 3.10 kg of a 15% by weight aqueous sodium peroxodisulfate solution and 1.05 kg of a 1% by weight aqueous ascorbic acid solution were used.

The throughput of the monomer solution was 20 t/h. The reaction solution had a feed temperature of 23.5° C.

The individual components were metered in the following amounts continuously into a List Contikneter continuous kneader reactor with a capacity of 6.3 m³ (LIST AG, Arisdorf, Switzerland):

| | |
|---|---|
| 20 t/h | of monomer solution |
| 40 kg/h | of polyethylene glycol-400 diacrylate |
| 82.6 kg/h | of hydrogen peroxide solution/sodium peroxodisulfate solution |
| 21 kg/h | of ascorbic acid solution |

Between the addition point for the crosslinker and the addition sites for the initiators, the monomer solution was inertized with nitrogen.

After about 50% of the dwell time there was an additional metered addition to the reactor of fines (1000 kg/h) which were obtained from the production process by grinding and sieving. The dwell time of the reaction mixture in the reactor was 15 minutes.

The aqueous polymer gel obtained was applied to the conveyor belt of an air circulation belt drier by means of an oscillating conveyor belt.

The air circulation belt drier had a length of 48 m. The conveyor belt of the air circulation belt drier had an effective width of 4.4 m.

The oscillating conveyor belt had a length of 5 m. The conveyor belt had a width of 0.8 m and an effective width of 0.5 m. The angle of repose of the aqueous polymer gel on the conveyor belt was about 15°. The cross section of the polymer gel bed on the conveyor belt was about 0.04 m². The speed of the conveyor belt was 0.5 m/s.

Proceeding from one end position, the oscillating conveyor belt was accelerated through a first pivot angle $\beta_1$ of 13° to an angular speed of 33°/s, decelerated through a second pivot angle $\beta_2$ of 20° to an angular speed of 17°/s and decelerated through a third pivot angle $\beta_3$ to the other end position. The total pivot angle was 50°. A double pass (from the first end position to the other end position and back) lasted about 7 s. The revolving conveyor belt had a surface of polytetrafluoroethylene (PTFE).

The temperature of the aqueous polymer gel on the oscillating conveyor belt was 90° C.

On the underside of the oscillating conveyor belt was a stripper device. The stripper device was a longitudinal scraper mounted transverse to the running direction of the revolving conveyor belt. The scraper was inclined at 20° against the running direction of the revolving conveyor belt. The distance of the stripper device from the discharge end was about 5 cm, meaning that the stripper device was in the region of the deflection roll. The distance of the stripper device from the revolving conveyor belt was 1 mm. The stripper device strips off aqueous polymer gel adhering to the outside of the revolving conveyor belt.

On the underside of the oscillating conveyor belt were additionally 3 two-phase nozzles. The two-phase nozzles were arranged transverse to the running direction of the conveyor belt. The distance between the two-phase nozzles was about 20 cm in each case. The distance of the two-phase nozzles from the discharge end was about 20 cm. The distance of the two-phase nozzles from the revolving conveyor belt was about 20 cm. A total of 10 kg/h of water and 100 kg/h of air were sprayed.

It was possible to efficiently clean the revolving conveyor belt by means of the stripper device. There was no significant caking at all on the conveyor belt over a period of 6 months.

On the air circulation belt drier, an air/gas mixture flowed continuously around the aqueous polymer gel and dried it. The dwell time in the air circulation belt drier was 37 minutes.

The dried polymer gel was ground and sieved to a particle size fraction of 150 to 850 μm.

The resulting water-absorbing polymer particles had a centrifuge retention capacity (CRC) of 34.9 g/g and an extractables content of 8.5% by weight.

Example 2 (Comparative Example)

The procedure was as in example 1, except that the spray nozzles on the oscillating conveyor belt were switched off.

It was possible to clean the revolving conveyor belt only with difficulty by means of the stripper device. There was significant caking on the conveyor belt, especially where polymer gel had already dried. After a few weeks of continuous production, the production had to be stopped and the conveyor belt cleaned, or the conveyor belt had to be exchanged owing to damage.

The invention claimed is:

1. A process for producing superabsorbent particles comprising polymerizing a monomer solution or suspension comprising
   a) at least one ethylenically unsaturated monomer which bears an acid group and is at least partly neutralized,
   b) at least one crosslinker,
   c) at least one initiator,
   d) optionally one or more ethylenically unsaturated monomer copolymerizable with the monomer mentioned under a), and
   e) optionally one or more water-soluble polymer,
   drying a resultant aqueous polymer gel in an air circulation belt drier, grinding, classifying, and optionally thermal surface postcrosslinking, wherein the aqueous polymer gel is introduced into the air circulation belt drier by an oscillating conveyor belt, the underside of the revolving oscillating conveyor belt is freed of adhering polymer gel by at least one stripper device, and the underside of the revolving oscillating conveyor belt is sprayed with 2 to 20 kg/h water by at least one spray nozzle.

2. The process according to claim 1, wherein the distance of the stripper device from a discharge end of the oscillating conveyor belt is less than 20% of the length of the oscillating conveyor belt, where the length of the oscillating conveyor belt is a distance of a pivot axis from the discharge end.

3. The process according to claim 1, wherein the stripper device mounted on the underside of the revolving oscillating conveyor belt is a scraper.

4. The process according to claim 3, wherein the scraper is inclined at 5° to 45° relative to the horizontal counter to the running direction of the oscillating conveyor belt.

5. The process according to claim 3, wherein a distance of the scraper from the underside of the revolving oscillating conveyor belt is from 0.1 to 5 mm.

6. The process according to claim 1, wherein a distance of the at least one spray nozzle from the discharge end of the oscillating conveyor belt is 1% to 50% of the length of the conveyor belt, where the length of the oscillating conveyor belt is a distance of a pivot axis from a discharge end.

7. The process according to claim 1, wherein a distance of the at least one spray nozzle from the conveyor belt is from 5 to 50 cm.

8. The process according to claim 1, wherein the water is sprayed onto the underside of the revolving oscillating conveyor belt by at least one two-phase nozzle.

9. The process according to claim 1, wherein the water is sprayed onto the underside of the revolving oscillating conveyor belt by at least one two-phase nozzle, and a weight ratio of atomizer gas to water is from 2 to 20.

10. The process according to claim 1, wherein the water is sprayed onto the underside of the revolving oscillating conveyor belt by at least two two-phase nozzles.

11. The process according to claim 1, wherein the at least one spray nozzle is beyond the stripper device in the running direction of the oscillating conveyor belt.

12. The process according to claim 1, wherein the conveyor belt has a length of 2 to 10 m, where the length of the oscillating conveyor belt is the distance of a pivot axis from a discharge end.

13. The process according to claim 1, wherein the surface of the oscillating conveyor belt at 23° C. has a contact angle with respect to water of at least 60°.

\* \* \* \* \*